US011969492B2

United States Patent
Petali et al.

(10) Patent No.: US 11,969,492 B2
(45) Date of Patent: Apr. 30, 2024

(54) COMPOSITION AND METHOD FOR SHAPING OR ALTERING THE SHAPE OF HAIR, METHOD FOR MANUFACTURING A COMPOSITION, KIT AND USES OF A COMPOSITION

(71) Applicant: L'OREAL, Paris (FR)

(72) Inventors: Érika Alegrio Jarque Petali, Rio de Janeiro (BR); Karima Abbas, Saint-Ouen (FR); Rosita Gonzalez, Rio de Janeiro (BR)

(73) Assignee: L'OREAL, Paris (FR)

( * ) Notice: Subject to any disclaimer, the term of this patent is extended or adjusted under 35 U.S.C. 154(b) by 171 days.

(21) Appl. No.: 17/279,151

(22) PCT Filed: Sep. 28, 2018

(86) PCT No.: PCT/BR2018/050354
§ 371 (c)(1),
(2) Date: Mar. 24, 2021

(87) PCT Pub. No.: WO2020/061656
PCT Pub. Date: Apr. 2, 2020

(65) Prior Publication Data
US 2021/0393492 A1    Dec. 23, 2021

(51) Int. Cl.
| A61K 8/22 | (2006.01) |
| A61K 8/06 | (2006.01) |
| A61K 8/34 | (2006.01) |
| A61K 8/368 | (2006.01) |
| A61K 8/41 | (2006.01) |
| A61K 8/55 | (2006.01) |
| A61Q 5/04 | (2006.01) |

(52) U.S. Cl.
CPC ............... *A61K 8/22* (2013.01); *A61K 8/062* (2013.01); *A61K 8/345* (2013.01); *A61K 8/368* (2013.01); *A61K 8/416* (2013.01); *A61K 8/55* (2013.01); *A61Q 5/04* (2013.01); *A61K 2800/805* (2013.01); *A61K 2800/884* (2013.01)

(58) Field of Classification Search
CPC .......... A61K 8/22; A61K 8/062; A61K 8/345; A61K 8/368; A61K 8/416; A61K 8/55; A61K 2800/805; A61K 2800/884; A61K 8/19; A61Q 5/04
USPC ....................................................... 424/70.2
See application file for complete search history.

(56) References Cited

FOREIGN PATENT DOCUMENTS

| EP | 1958610 A2 | 8/2008 | |
| FR | 2912309 A1 * | 8/2008 | .......... A61K 8/8152 |
| FR | 2966729 A1 * | 5/2012 | ............. A61K 8/046 |
| WO | WO-2016098786 A1 * | 6/2016 | ............. A61K 8/062 |

OTHER PUBLICATIONS

International Search Report and Written Opinion dated Jul. 2, 2019, for corresponding PCT Application No. PCT/BR2018/050354.
Database GNPD; Mintel "Conditioning Cream Neutralizer," 2015 XP055596271.

* cited by examiner

*Primary Examiner* — Frederick F Krass
*Assistant Examiner* — Lucy M Tien
(74) *Attorney, Agent, or Firm* — POLSINELLI PC (57) ABSTRACT

The present application relates to a composition comprising at least one neutralizing agent, at least one stabilizing agent, at least three chelator agents and at least one cationic agent. Also, the present invention is related to a method for manufacturing the composition, a method for applying the composition onto keratin fibers for shaping or altering the shape of the keratin fibers, particularly hair, a kit that is suitable for performing the claimed method for shaping or altering the shape of the hair and the use of the claimed composition for shaping or altering the shape of the hair.

19 Claims, 10 Drawing Sheets

COMPOSITION AND METHOD FOR SHAPING OR ALTERING THE SHAPE OF HAIR, METHOD FOR MANUFACTURING A COMPOSITION, KIT AND USES OF A COMPOSITION

CROSS-REFERENCE TO RELATED APPLICATIONS

This application is a national stage application (under 35 U.S.C. § 371) of PCT/BR2018/050354, filed Sep. 28, 2018, which is incorporated herein by reference in its entirety.

FIELD OF THE INVENTION

The present application relates to a composition comprising at least one neutralizing agent, at least one stabilizing agent, at least three chelator agents and at least one cationic agent. Also, the present invention is related to a method for manufacturing the composition, a method for applying the composition onto keratin fibers for shaping or altering the shape of the keratin fibers, particularly hair, a kit that is suitable for performing the claimed method for shaping or altering the shape of the hair and the use of the claimed composition for shaping or altering the shape of the hair.

BACKGROUND OF THE INVENTION

Seeking to have a perfect appearance of the hair, people are often reshaping their hair, in particular curly or wavy hair, by means of straightening processes in order to shape or alter the shape of the hair.

For this reason, researchers are always working on the development of new hair straightening products, that do not damage the hair fibers while changing the appearance, shape or configuration of the hair. Examples of such hair cosmetic products are hair relaxers or hair straighteners which can relax or straighten curly or kinky hair, including wavy hair. Hair relaxers may either be applied in a hair salon by a professional or at home by the individual consumer. Straightening or relaxing the curls of very curly hair may increase the manageability and ease of styling of such hair.

In traditional straightening processes, a first step (reduction step) is performed on the hair, wherein the disulfide bonds of the keratin are opened by the use of an alkaline composition, usually comprising a sulfur-based reducing agent. The reduction step involves hydrolyzing the keratin of the hair with various alkaline agents, such as inorganic hydroxides, for instance sodium hydroxide, or organic hydroxides, such as guanidine hydroxide, or organic amines. The hair must, then, be rinsed. In a second step (oxidizing step, also known as reconstructing, fixing or neutralizing step), the disulfide bonds must be reconstructed by a neutralizing composition (oxidizing composition) to result in the desired shape of the hair. The new shape given to the hair by such a chemical treatment is eminently long-lasting and especially withstands washing with water or shampoos.

The products intended for straightening or uncurling used in the first step are generally formulated either using very alkaline compositions, with a pH above 12, or using a high concentration of thiols, such as mercaptan compounds. The oxidizing compositions required for performing the second step are usually compositions based on aqueous hydrogen peroxide solution.

The reducing agents of the first step are generally used in high concentrations, which may lead to more or less pronounced degradation of the keratin fiber, in particular when the hair is dyed. Also, it is known that the use of these reducing agents or of these strong alkaline agents can lead to scalp discomfort (irritation, itching, etc.). In addition, due to the very reactive nature of the hydrogen peroxide used in the second step, the neutralizing composition of the state of the art is very simple and very fluid, making it impossible to formulate a neutralizing composition that is easier to apply (less runny), and that provides cosmetic properties to the hair while keeping the concentration of the hydrogen peroxide stable enough to enable the neutralization of the fibers.

Therefore, there is a necessity for new neutralizing compositions for shaping or altering the shape of keratin fibers, particularly hair, that are capable of neutralizing and treating the hair, not having the drawbacks of the commonly used compositions, that is, which do not run during the application, and that maintain the concentration of hydrogen peroxide.

The Applicant has surprisingly developed a new composition for neutralizing keratin fibers comprising hydrogen peroxide in the form of a neutralizing mask, which is easier to apply, and that is stable enough to comprise hydrogen peroxide and other components that treat the hair during the second step of a straightening process.

SUMMARY OF THE INVENTION

The present invention is directed to provide a new neutralizer composition, in the form of a mask, for shaping or altering the shape of keratin fibers, particularly hair, comprising at least one neutralizing agent, at least one stabilizing agent, at least three chelator agents and at least one cationic agent.

It is an objective of the present invention to provide a stable composition having hydrogen peroxide that not only neutralizes the keratin fibers which have already undergone the first step of a conventional straightening process, but also having cosmetic properties that treat such fibers. The new neutralizing composition of the present invention, allows the hydrogen peroxide to be stable in the presence of cationic compounds and of additional ingredients that treat the hair.

Particularly, it was surprisingly and unexpectedly discovered that the substitution of the behentrimonium chloride which is present in the conventional neutralizing compositions by an association of behentrimonium chloride with at least one stabilizing agent, made it possible to formulate a new galenic form for a neutralizing composition, which does not only neutralize the hair, but also allows the inclusion of additional ingredients to the composition in order to improve its cosmeticity, allowing the neutralizing composition to comprise ingredients that also treat the hair undergoing a straightening process, resulting in effectively shaped or straightened hair.

The new neutralizing composition of the present invention remains on the hair for a predetermined period of time as to achieve the desired shape of the hair or desired degree of straightening of the hair, due to their more consistent viscosity (not run).

In other words, the inventors of the present application have surprisingly developed a new and improved neutralizing composition comprising hydrogen peroxide which is stable and treats the hair during a straightening process.

BRIEF DESCRIPTION OF THE DRAWING

FIG. 1 (*a*) to FIG. 10 (*d*) show images of 10 volunteers whose hairs have been treated with the inventive composition (left side of the image, under "tested") and with the composition of the state of the art (right side of the image, under "reference"). Figure (a) are related to the hair before the treatment with the compositions (natural hair), Figure (b) are related to the straightened hair after the treatment, Figure (c) are related to the straightened hair in the first return of the volunteer (after 2 weeks), and Figure (d) are related to the straightened hair in the second return of the volunteer (after 5 weeks).

DETAILED DESCRIPTION OF THE INVENTION

A suitable neutralizing composition according to the present invention comprises:
 (a) a neutralizing agent selected from hydrogen peroxide;
 (b) at least one stabilizing agent selected from dipropylene glycol, propylene glycol, glycerin, caprylyl glycol and their mixtures;
 (c) at least three chelator agents selected from tetrasodium etidronate, tetrasodium pyrophosphate, sodium salicylate and their mixtures; and
 (d) at least one cationic agent.

The composition according to the invention provides neutralization of the keratin fibers in a straightening process, while also treating such fibers from the damages provoked by the first reducing step.

In a preferred embodiment, the neutralizing agent is present in the composition of the present invention in an amount ranging from about 0.65% to 3.4% by weight and preferably from about 1.5% to 3% by weight, or more preferably from about 2.3% to 2.6% by weight, including all ranges and sub-ranges there between, relative to the total weight of the composition.

In a preferred embodiment, the stabilizing agent used in the present invention is present in an amount ranging from about 0.4% to 10% by weight and preferably from about 0.45% to 8% by weight, or more preferably from about 0.5% to 7.3% by weight, including all ranges and sub-ranges there between, relative to the total weight of the composition.

In a preferred embodiment, the at least three chelator agents used in the present invention are in an amount ranging from about 0.03% to 1% by weight and preferably from about 0.06% to 0.6% by weight, or more preferably from about 0.1% to 0.2% by weight, including all ranges and sub-ranges there between, relative to the total weight of the composition.

The at least three chelator agents employs a first chelator in an amount preferably ranging from about 0.01% to about 0.6% by weight and preferably from about 0.04% to about 0.5% by weight, or more preferably from about 0.06% to about 0.1% by weight, including all ranges and sub-ranges there between, relative to the total weight of the composition.

The at least three chelator agents employs a second chelator in an amount preferably ranging from about 0.01% to about 0.5% by weight and preferably from about 0.02% to about 0.3% by weight, or more preferably from about 0.03% to about 0.1% by weight, including all ranges and sub-ranges there between, relative to the total weight of the composition.

The at least three chelator agents employs a third chelator in an amount preferably ranging from about 0.01% to about 0.3% by weight and preferably from about 0.025% to about 0.2% by weight, or more preferably from about 0.03% to about 0.1% by weight, including all ranges and sub-ranges there between, relative to the total weight of the composition.

In a preferred embodiment, the cationic agent used in the present invention is in an amount ranging from about 0.5% to about 5% by weight and preferably from about 1% to 4.7% by weight, or more preferably from about 1.2% to 4.4% by weight, including all ranges and sub-ranges there between, relative to the total weight of the composition.

The pH of the composition of the invention is preferably ranging of about 2 to less than 7, more preferably, of about 2.5 to about 6.5.

The viscosity of the composition of the invention is preferably within the range of about 12.4 P to about 21.3 P (from about 30 UD to about 50 UD), measured by a Rheomat 180, spindle No. 3, for 30 seconds at 25° C.

In a preferred embodiment, the composition of the present invention is in the form of an O/W emulsion.

In another preferred embodiment the invention is related to a kit for shaping or altering the shape of hair, that comprises a standard reducing composition and a neutralizing composition of the present invention.

Standard reducing compositions intended for smoothing or perming the hair generally include reducing agents in the form of sulfites, bisulfites, alkylphosphines or, preferably, thiols. These reducing compositions are generally in the form of a thickened or unthickened lotion, a cream or a gel.

Cationic Agents

The cationic surfactant according to the present invention may be chosen from alkyl quaternary ammonium compounds such as behentrimonium chloride, cetrimonium chloride, quaternium-22, behenylamidopropyl-2, 3-di-hydroxypropyldimethylammonium chloride, palmitylamidopropyltrimethylammonium chloride, and chloride and methyl sulfate of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of monoacyloxyethyl-hydroxyethyl-dimethyl-ammonium, distearyldimethylammonium chloride, oleocetyldimethylhydroxyethylammonium chloride, stearamidopropyldimethyl (myristyl acetate) ammonium chloride, di(C1-C2 alkyl) (C12-C22 alkyl)hydroxy(C1-C2alkyl)ammonium salt, or alkyltrimethylammonium salt in which the alkyl radical comprises 12 to 24 carbon atoms, propanetallowdiammonium dichloride, behentrimonium methosulfate, quaternium-83, quaternium-87, and mixtures thereof.

The cationic surfactants may also be chosen from fatty dialkylamines. In some instances, the fatty dialkylamines correspond to the compounds of formula:

$$RN(R')_2 \qquad (A)$$

wherein R is a fatty group containing at least 6 carbon atoms (and up to 30 carbon atoms) In addition, R can be linear or branched, saturated or unsaturated, and substituted or unsubstituted. Typically, R is a linear or branched, acyclic alkyl or alkenyl group; and the groups R', which may be identical or different, represent a hydrocarbon radical containing less than 6 carbon atoms. In addition, the groups R', which may be identical or different, are linear or branched, saturated or unsaturated, and substituted or unsubstituted. Preferably, the groups R' are methyl groups. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, stearyl dimethyl amine, and mixtures thereof.

Further, the cationic surfactants may be selected from fatty amidoamine compounds corresponding to compounds of the following formula and their salts:

RCONHR"N(R')$_2$ (B)

wherein R is a fatty group containing at least 6 carbon atoms (and up to 30 carbon atoms). In addition, R can be linear or branched, saturated or unsaturated, and substituted or unsubstituted. Typically, R is a linear or branched, acyclic alkyl or alkenyl group; R" is a divalent hydrocarbon radical containing less than 6 carbon atoms, preferably 2 or 3 carbon atoms, and the groups R', which may be identical or different, represent a hydrocarbon radical containing less than 6 carbon atoms. In addition, the groups R', which may be identical or different, are linear or branched, saturated or unsaturated, substituted or unsubstituted. Preferably, the groups R' are methyl groups. Non-limiting examples include oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palmitamidopropyl dimethylamine, stearamidoethyldiethylamine, stearyl dimethyl amine, brassicamidopropyl dimethylamine, and mixtures thereof.

Terms

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about", meaning within +/−10% of the indicated number.

As used herein, all ranges provided are meant to include every specific range within, and combination of sub ranges between, the given ranges. Thus, a range from 1 to 5, includes specifically 1, 2, 3, 4 and 5, as well as sub ranges such as 2 to 5, 3 to 5, 2 to 3, 2 to 4, 1 to 4, etc. All ranges and values disclosed herein are inclusive and combinable. For examples, any value or point described herein that falls within a range described herein can serve as a minimum or maximum value to derive a sub-range, etc.

All numbers expressing pH values are to be understood as being modified in all instances by the term "about" which encompasses up to +/−3%.

The compositions and processes of the present invention can comprise, consist of, or consist essentially of the essential elements and limitations of the invention described herein, as well as any additional or optional ingredients, components, or limitations described herein or otherwise useful.

Additional Fatty Substances

The present invention may employ at least one fatty substance. The term "fatty substance" means an organic compound that is insoluble in water at ordinary room temperature (25 degrees centigrade) and at atmospheric pressure (760 mmHg) (solubility of less than 5 percent, preferably 1 percent and even more preferentially 0.1 percent). They have in their structure at least one hydrocarbon-based chain containing at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane.

The fatty substance may be selected from alkanes, esters of fatty acid, esters of fatty alcohol, hydrocarbons, silicones, nonsilicone waxes, mineral oils, vegetable oils, non-silicone synthetic oils, fatty alcohols, and mixtures thereof.

The fatty substances are especially chosen from $C_6$-$C_{16}$ hydrocarbons, hydrocarbons containing more than 16 carbon atoms and in particular alkanes, oils of animal origin, oils of plant origin, glycerides or fluoro oils of synthetic origin, fatty acid and/or fatty alcohol esters, non-silicone waxes and silicones.

The fatty esters and fatty acids more particularly contain one or more linear or branched, saturated or unsaturated hydrocarbon-based groups comprising 6 to 30 carbon atoms, which are optionally substituted, in particular with one or more (in particular 1 to 4) hydroxyl groups. If they are unsaturated, these compounds may comprise one to three conjugated or unconjugated carbon-carbon double bonds.

As regards the $C_6$-$C_{16}$ alkanes, they are linear, branched or possibly cyclic. Mention may be made, by way of example, of hexane, dodecane or isoparaffins, such as isohexadecane or isodecane. The linear or branched hydrocarbons containing more than 16 carbon atoms may be chosen from liquid paraffins, petroleum jelly, liquid petroleum jelly, polydecenes, and hydrogenated polyisobutene such as Parleam®.

Among the animal oils, mention may be made of perhydrosqualene.

Among the triglycerides of plant or synthetic origin, mention may be made of liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, sunflower oil, castor oil, avocado oil, jojoba oil, shea butter oil and caprylic/capric acid triglycerides, for instance those sold by the company Stearineries Dubois or those sold under the names Miglyol® 810, 812 and 818 by the company Dynamit Nobel.

Among the fluoro oils, mention may be made of perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-(trifluoromethyl)perfluoromorpholine sold under the name PF 5052® by the company 3M.

The wax(es) that may be used in the anhydrous cosmetic composition (I) are chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

As regards the esters of a fatty acid and/or of a fatty alcohol, which are advantageously different from the triglycerides mentioned above, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononanoate; octyl 5 palmitate; octyl pelargonate; octyl stearate; octyldodecyl erucate; oleyl erucate; ethyl and isopropyl palmitates; 2-ethylhexyl palmitate; 2-octyldecyl palmitate; alkyl myristates, such as isopropyl, butyl, cetyl, 2-octyldodecyl, myristyl or stearyl myristate; hexyl stearate; butyl stearate; isobutyl stearate; dioctyl malate; hexyl laurate or 2-hexyldecyl laurate.

The fatty alcohols that may be used in the composition may be chosen from alcohols of formula R'OH, in which R' denotes a saturated or unsaturated, linear or branched radical, comprising from 6 to 40 carbon atoms and more particularly from 8 to 30 carbon atoms. Examples that may be mentioned include cetyl alcohol, stearyl alcohol and the mixture thereof (cetearyl alcohol), octyldodecanol, 2-butyloctanol, 2-hexyldecanol, 2-undecylpentadecanol, oleyl alcohol, lauryl alcohol, behenyl alcohol and linoleyl alcohol.

The fatty substance can be employed in the composition of the present invention in an amount of from about 1% to about 15% by weight, preferably from about 1.5% to about 12.5% by weight, more preferably from about 1.85% to about 10.5% by weight, based on the total weight of the composition, including all ranges and subranges therebetween.

Water

The compositions of the present invention comprise water. Water can be present in the amount of about 95% to about 5% by weight or less, relative the total weight of the compositions. Additionally, water can be present in the compositions of the present invention in the amount of from about 20% to about 95% by weight, or from about 50% to about 90% by weight, or from about 60% to about 88% by weight, relative to the weight of the compositions.

Cosmetically Acceptable Solvent

The compositions of the present invention may further comprise at least one cosmetically acceptable solvent chosen from organic solvents.

Suitable organic solvents may be chosen from volatile and nonvolatile organic solvents.

Suitable organic solvents are typically $C_2$-$C_8$ alcohols, glycols, polyols, polyol ethers, glycol ethers, glycerin, hydrocarbons, oils, and mixtures thereof. Examples of organic solvents include, but are not limited to, ethanol, isopropyl alcohol, benzyl alcohol, phenyl ethyl alcohol, propylene glycol, pentylene glycol, hexylene glycol, glycerol, and mixtures thereof.

Other suitable organic solvents include glycol ethers, for example, ethylene glycol and its ethers such as ethylene glycol monomethyl ether, ethylene glycol monopropyl ether, ethylene glycol monobutyl ether, propylene glycol and its ethers, such as propylene glycol monomethyl ether, propylene glycol monopropyl ether, propylene glycol monobutyl ether, dipropylene glycol and diethylene glycol alkyl ethers, such as diethylene glycol monoethyl ether, diethylene glycolmonobutyl ether, and dipropylene glycol n-butyl ether. Glycol ethers are commercially available from The Dow Chemical Company under the DOW E-series and DOW P-series. One preferred glycol ether for use in the present invention is dipropylene glycol n-butyl ether, known under the tradename of DOWANOL™ DPnB.

Suitable organic solvents also include synthetic oils and hydrocarbon oils include mineral oil, petrolatum, and $C_{10}$-$C_{40}$ hydrocarbons which may be aliphatic (with a straight, branched or cyclic chain), aromatic, arylaliphatic such as paraffins, iso-paraffins, isododecanes, aromatic hydrocarbons, polybutene, hydrogenated polyisobutene, hydrogenated polydecene, polydecene, squalene, petrolatum and isoparaffins, silicone oils, fluoro oils and mixtures, thereof.

The term "hydrocarbon-based oil" or "hydrocarbon oil" refers to oil mainly containing hydrogen and carbon atoms and possibly oxygen, nitrogen, sulfur and/or phosphorus atoms. Representative examples of hydrocarbon-based oils include oils containing from 8 to 16 carbon atoms, and especially branched C8-C16 alkanes (also known as isoparaffins), for instance isododecane (also known as 2,2,4,4,6-pentamethylheptane), isodecane and isohexadecane.

Examples of silicone oils that may be useful in the present invention include nonvolatile silicone oils such as polydimethylsiloxanes (PDMS), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, and dimethicones or phenyltrimethicones with a viscosity of less than or equal to 100 cSt.

Other representative examples of silicone oils that may be useful in the present invention include volatile silicone oils such as linear or cyclic silicone oils, especially those with a viscosity in centistokes ($8 \times 10^{-6}$ m$^2$/s) and especially containing from 2 to 10 silicon atoms and in particular from 2 to 7 silicon atoms, these silicones optionally comprising alkyl or alkoxy groups containing from 1 to 10 carbon atoms. Specific examples include dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Representative examples of fluoro oils that may be suitable for use in the present invention include volatile fluoro oils such as nonafluoromethoxybutane and perfluoro-methylcyclopentane.

The amount of the organic solvent/compound present in the compositions of the present invention can range from about 0.5% to about 60%, or from about 0.5% to about 40%, or from about 0.5% to about 30%, or from about 0.5% to about 20%, and in some embodiments, from about 0.5% to about 15%, by weight, or preferably from about 1% to about 10%, by weight, or more preferably from about 1.5% to about 8%, by weight, or from about 2% to about 6%, by weight, including all ranges and subranges there-between, relative to the total weight of the composition.

In some embodiments, the amount of the organic solvent/compound present in the compositions of the present invention is at about 2%, about 2.5%, about 3%, about 3.5%, about 4%, about 4.5%, about 5%, about 5.5% or about 6% by weight, including all ranges and subranges there-between, relative to the total weight of the composition.

In certain embodiments, compositions of the present invention comprise both water and organic solvents/compounds selected from volatile organic solvents, non-volatile organic solvents, and mixtures thereof.

Preferred examples of organic solvents/compounds include volatile organic solvents such as $C_2$ to $C_4$ mono-alcohols, such as ethanol, isopropyl alcohol, butanol, polyols such as $C_2$-$C_6$ glycols e.g., propylene glycol, butylene glycol, pentylene glycol, hexylene glycol, glycerol, isododecane, volatile polyol ethers, volatile glycol ethers, acetone, propylene carbonate, benzyl alcohol, and mixtures thereof. In certain embodiments, it is preferred that the amount of volatile organic solvent/compound does not exceed 55% by weight, relative to the weight of the composition of the present invention.

In other certain embodiments, it is preferred that the amount of volatile organic solvent/compound does not exceed 20% by weight, relative to the weight of the composition of the present invention.

In yet other certain embodiments, it is preferred that the amount of volatile organic solvent/compound does not exceed 10% by weight, relative to the weight of the composition of the present invention.

In preferred embodiments, the amount of volatile organic solvent/compound does not exceed 6% by weight, relative to the weight of the composition of the present invention.

Other preferred examples of organic solvents/compounds include nonvolatile organic solvents such as hydrocarbons such as straight chain hydrocarbons, nonvolatile silicone oils, mineral oil, polybutene, hydrogenated polyisobutene, hydrogenated polydecene, polydecene, squalene, petrolatum, isoparaffins, nonvolatile glycol ethers, and mixtures, thereof.

In certain embodiments, it is preferred that the amount of nonvolatile organic solvent/compound does not exceed 40% by weight, relative to the weight of the composition of the present invention.

In other certain embodiments, it is preferred that the amount of nonvolatile organic solvent/compound does not exceed 20% by weight, relative to the weight of the composition of the present invention.

In yet other certain embodiments, it is preferred that the amount of nonvolatile organic solvent/compound does not exceed 10% by weight, relative to the weight of the composition of the present invention.

In certain embodiments of the present invention, the at least one organic solvent is chosen from ethanol.

Additional Ingredients

The compositions according to the invention may further comprise any additional ingredient usually used in the field under consideration, selected, for example, from thickening agents, conditioning agents, natural and synthetic oils, humectants, shine agents, fillers, colorants, pigments, chelating agents, sequestering agents, fragrances, preservatives, stabilizers, silicones, polymers, vitamins, surfactants, buffers and mixtures thereof.

The additional ingredients may represent from 10% to 30%, such as from 15% to 25% or such as from 10 to 20% by weight of the total weight of the composition of the invention.

It is a matter of routine operations for a person skilled in the art to adjust the nature and amount of the additives present in the compositions in accordance with the invention such that the desired cosmetic properties and stability properties thereof are not thereby affected.

METHOD FOR SHAPING OR ALTERING THE SHAPE OF HAIR

In an embodiment, the present invention relates to a process for straightening hair comprising the steps of:
(a) Contacting hair with a shampoo having a neutral pH;
(b) Drying the hair;
(c) Applying onto the hair a standard reducing composition (first step of a straightening process);
(d) Leaving the standard reducing composition onto the hair for approximately 30 minutes in a plastic Cap;
(e) Rinsing the hair with water;
(f) Drying the hair;
(g) Straightening the hair with a flat iron;
(h) Applying onto the hair the inventive neutralizing composition, according to the present invention (second step of a straightening process);
(i) Leaving the neutralizing composition into the hair for approximately 10 minutes;
(j) Rinsing the hair with water;
(k) Washing the hair with an intermediate agent having a neutral pH and selected from a shampoo and/or a conditioner, followed by rinsing with water.

In certain embodiments, the straightening step in the above-described process is preferably accomplished by use of a device such as a heating flat iron device, a blow dryer, or a hair dryer. When a hair dryer or blow dryer is used, a brush or comb may be passed one or more times over or through the hair.

The straightening step in the above-described process may also be accompanied by a smoothing action on the hair, preferably performed with a mechanical or physical device, for example, the plates of a flat iron or a hair brush.

In certain embodiments, the straightening step of the above-described process is accomplished at a temperature higher than 100° C.

In certain embodiments, the composition of the above-described process of the invention is allowed to remain on the hair for a predetermined amount of time sufficient to shape or alter the shape of the hair.

The composition in the above-described process is stable over time, that is, it does not exhibit phase separation and it can be stored for several months without modification and with very little change or fluctuation in the viscosity and/or rheology and pH of the composition.

Preferably, before the composition in the process above is applied onto the hair, said hair is first contacted with a shampoo having a neutral pH and then rinsed with water.

In certain embodiments, the intermediate agent in the process above is a shampoo or conditioner, preferably having a neutral pH.

In certain processes, the composition is allowed to remain (leave-on time) on the keratin fibers for a pre-determined amount of time, for example, from about 1 to about 60 minutes, or such as from about 5 to about 45 minutes, or such as from about 5 to about 30 minutes, or such as from about 10 to about 20 minutes, or such as at about 20 minutes, or such as at about 10 minutes. The pre-determined amount of time is sufficient to achieve satisfactory straightening or shaping or altering the shape of the keratin fibers such as hair on the human head.

In other embodiments, the composition is rinsed from the hair with water before brushing the hair. The rinsed hair may also be subjected to a detangling or smoothing action before brushing the hair.

Suitable devices for detangling or brushing or smoothing the hair include a hair brush, comb, or heating flat iron. The smoothing or detangling action on the hair may also include running the fingers through the hair.

The composition can also be applied onto the hair using an applicator device or with the hands or gloved hands.

A suitable applicator device is an applicator brush or applicator comb or applicator spatula or a dispenser or applicator tip attached to the container holding the composition.

Heat (at a temperature of at least 40° C.) can be applied to the hair while the smoothing action is performed on the hair. The heat source can be chosen from a blow dryer, a flat iron, a hair dryer, a heat lamp, a heat wand, or other similar devices.

In addition, independently of the embodiment use, the composition present on the fibers or hair is left in place for a time, generally, from about 1 minute to about 60 minutes, such as from about 5 minutes to about 45 minutes, or such as from about 5 minutes to about 20 minutes, or such as from about 10 minutes to about 20 minutes, or such as of about 20 minutes or such as of about 10 minutes.

The straightening effects obtained using the composition and process of the present disclosure may also be durable or wash resistant.

The composition of the present invention may be packaged in any suitable container such as a tube, a jar or a bottle. In certain embodiments, the composition can be packaged in a tube or bottle, for example, a squeeze tube or squeeze bottle. Additionally, an applicator device can be attached or connected to the opening of the packaging/squeeze tube or bottle wherein the applicator device is a brush or a comb with teeth such that the ends of the teeth have openings from which the composition of the invention can flow through and be applied directly onto the hair.

As used herein, the process and composition disclosed herein may be used on the hair that has not been artificially dyed, pigmented or permed.

As used herein, the process and composition disclosed herein may be also used on the hair that has been artificially dyed, pigmented or permed.

METHOD FOR MANUFACTURING A COMPOSITION

The compositions of the present invention are achieved by combining at least one neutralizing agent, at least one stabilizing agent, at least three chelator agents, and at least one cationic agent.

In one embodiment, the method of making the compositions of the present invention comprises the steps of:

Step (1)—Preparation of the water phase
(a) Adding water (25% by weight, relative to the total weight of the composition);
(b) Adding the additive(s), such as preservative(s) and chelant(s);
(c) Mixing well and heating to 60° C.;
(d) Adding at least one rheologic agent (additive);
(e) Mixing well;

Step (2)—Preparation of the oil phase
(f) Adding the fatty alcohol(s), the cationic agent(s) and the fatty compound(s);
(g) Mixing well and heating to 70° C.;

Step (3)—Preparation of the emulsion
(h) Adding the water phase to the oil phase, followed by adding nonionic surfactants to the obtained mixture, and mixing until forming the emulsion;

Step (4)—Addition of the remaining ingredients to the emulsion
(i) Adding water (30% by weight, relative to the total weight of the composition);
(j) Mixing and allowing the mixture to cool;
(k) Adding hydrogen peroxide, silicones and at other optional additives, such as a pH adjuster (such as phosphoric acid);
(l) Mixing;
(m) Adding water (Q.S.);
(n) Mixing and allowing the mixture to cool, if necessary;
(o) Controlling pH and adjusting it, if necessary; and
(p) Mixing until homogeneous.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result.

EXAMPLES

The following Examples are intended to be non-restrictive and explanatory only, with the scope of the invention being defined by the claims.

The ingredient amounts in the compositions/formulas described below are expressed in % by weight, based on the total weight of the composition/formula.

Examples 1 to 9

Suitable compositions according to the state of the art are as Examples 1 and 2, and suitable compositions according to the present invention are as Examples 3 to 9, as follows:

TABLE 1

Comparison between the compositions of the state of the art and of the present invention

| FUNCTION | INGREDIENT | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|
| Nonionic surfactants | Trideceth-15 Trideceth-3 Trideceth-6 | 5 | — | 0.87 | 0.2 | — | 0.06 | — | 0.15 | 0.15 |

TABLE 1-continued

Comparison between the compositions of the state of the art and of the present invention

| FUNCTION | INGREDIENT | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|
| | Trideceth-5 | | | | | | | | | |
| | Trideceth-10 | | | | | | | | | |
| | Steareth-2 | | | | | | | | | |
| Fatty alcohols | Stearyl alcohol | — | 12.15 | 7 | 8 | 9 | 6 | 4 | 6 | 6 |
| | Cetearyl alcohol | | | | | | | | | |
| Silicones | Bis-cetearyl amodimethicone | — | — | 1.75 | 7.5 | — | — | 1.8 | 1.7 | 1.7 |
| | Dimethicone | | | | | | | | | |
| | Amodimethicone | | | | | | | | | |
| Fatty compounds | Cetyl esters | — | 4.1 | 2.1 | 1.9 | 1.8 | 0.9 | 2 | — | — |
| | Mineral oil | | | | | | | | | |
| Cationic agents | Behentrimonium chloride | 0.79 | 2.16 | 5 | 3 | 3.1 | 1.75 | 3 | 3.375 | 2.7 |
| | Cetrimonium chloride | | | | | | | | | |
| | Hydroxypropyltrimonium hydrolyzed wheat protein | | | | | | | | | |
| | Behentrimonium methosulfate | | | | | | | | | |
| | Dipalmitoylethyl hydroxyethylmonium methosulfate | | | | | | | | | |
| | Quaternium-87 | | | | | | | | | |
| Additives | Tocopherol | 0.22 | 0.02 | 0.44 | 0.35 | 2.4 | 0.2 | 0.05 | 0.25 | 0.75 |
| | Panthenol | | | | | | | | | |
| | Tocopheryl acetate | | | | | | | | | |
| | Phosphoric acid | | | | | | | | | |
| | Chlorhexidine digluconate | | | | | | | | | |
| | Benzophenone-4 | | | | | | | | | |
| | Ethylexyl methoxycinnamate | | | | | | | | | |
| | Hydrogenated polyisobutene | | | | | | | | | |
| | Hydroxyethylcellulose | | | | | | | | | |
| | Hydroxypropyl guar | | | | | | | | | |
| | Phenoxyethanol | | | | | | | | | |
| | BHT | | | | | | | | | |
| | Acetic acid | | | | | | | | | |
| | Isopropyl alcohol | | | | | | | | | |
| | hydroxypropyl guar hydroxypropyltrimonium chloride | | | | | | | | | |
| Active compounds | Magnesium sulfate | 2.4 | 2.8 | 2.9 | 2 | 0.76 | 2.35 | 2.85 | 4.15 | 2.46 |
| | Potassium hydroxide | | | | | | | | | |
| | Hydrogen peroxide | | | | | | | | | |
| | Sodium PCA | | | | | | | | | |
| | Arginine | | | | | | | | | |
| | Serine | | | | | | | | | |
| | Glutamic acid | | | | | | | | | |
| | 2-oleamido-1,3-octadecanediol | | | | | | | | | |
| | Citric acid | | | | | | | | | |
| Stabilizing agent | Dipropylene glycol | — | — | 1.9 | 2 | 0.8 | 1.5 | 1 | 0.5 | 0.55 |
| | Propylene glycol | — | — | — | — | 1 | — | 0.3 | — | — |
| | Caprylyl glycol | — | — | — | — | 0.5 | — | — | 0.5 | — |
| | Glycerin | 1.5 | — | 6 | 2 | 5 | — | — | — | — |
| Chelator agent | Tetrasodium etidronate | 0.135 | 0.135 | 0.135 | 0.135 | 0.135 | 0.135 | 0.135 | 0.135 | 0.135 |
| | Tetrasodium pyrophosphate | | | | | | | | | |
| | Sodium salicylate | | | | | | | | | |
| Other additives | plant extracts, plant oils, pH adjusters | <0.5 | <0.5 | <0.5 | <0.5 | <0.5 | <0.5 | <0.5 | <0.5 | <0.5 |
| Solvent | Water | Q.S. | Q.S. | Q.S. | Q.S. | Q.S. | Q.S. | Q.S. | Q.S. | Q.S. |

Example 10

Assessments of Straightening Performance and Reduction of Frizziness and Volume of Hair A comparative essay was performed between the neutralizing composition according to the present invention (Ex. 9) and a neutralizing composition of the state of the art (Ex. 1), wherein each composition was applied on half of the hair (half head) of each of the 10 volunteers with natural and/or damaged hair of types III and IV (curly and wavy hair), leaving a small lock of natural hair in the middle without the application of any one of the compositions.

The straightening performance on such different types of hair was visually assessed for the following attributes: reduction of the volume (width) of the hair (also indicative of the degree of frizziness of and degree of discipline of the hair) and degree of straightening of the hair swatch.

A panel of experts analyzed the hair before and after the application of the compositions of the present invention and of the state of the art, and during both returns of the volunteers.

Figure 1:
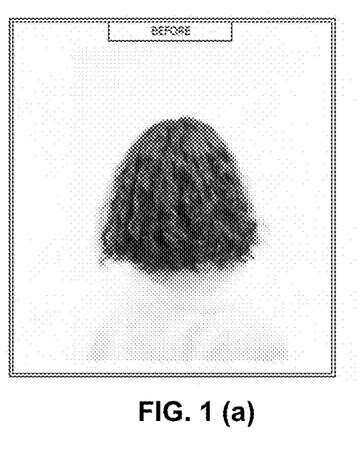
Figure 2:
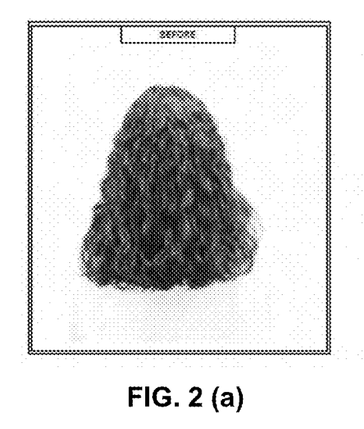
Figure 3:
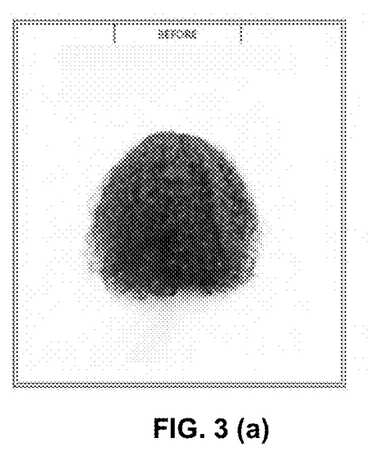
Figure 4:
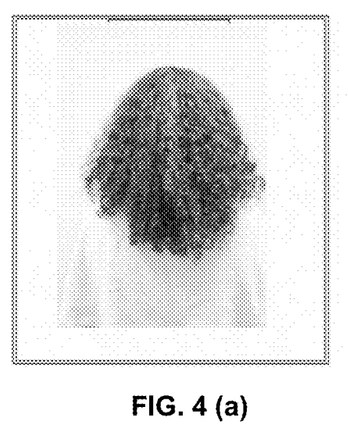
Figure 5:
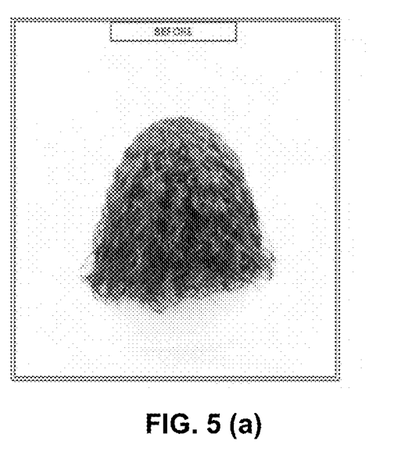
Figure 6:
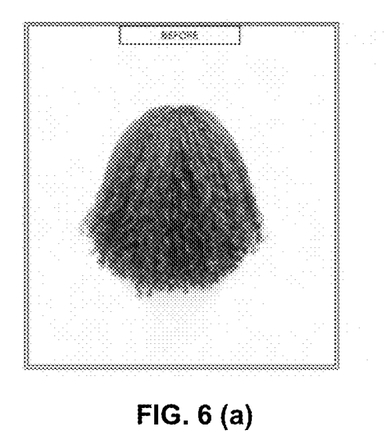
Figure 7:
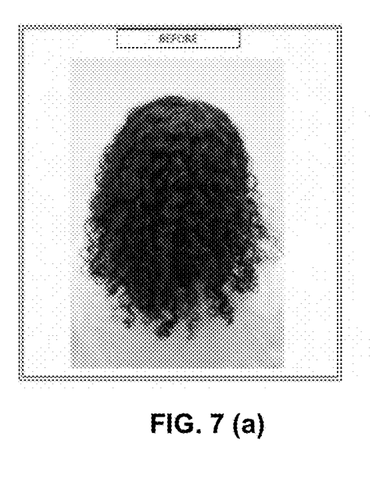
Figure 8:
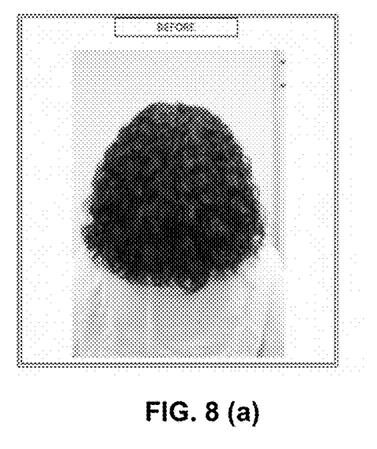
Figure 9:
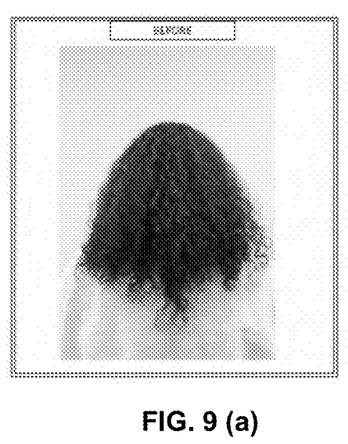
Figure 10:
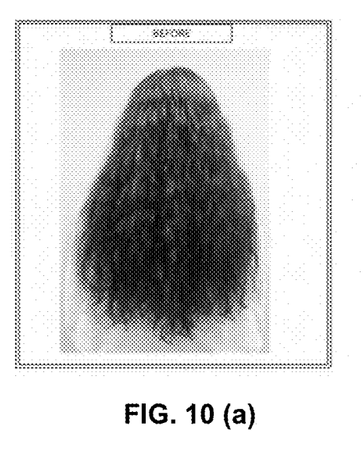

FIG. 1 (a) to FIG. 10 (d) show images of 10 volunteers whose hairs have been treated with the inventive composition (left side of the image, under "tested") and with the composition of the state of the art (right side of the image, under "reference"). Figure (a) are related to the hair before the treatment with the compositions (natural hair), Figure (b) are related to the straightened hair after the treatment, Figure (c) are related to the straightened hair in the first return of the volunteer (after 2 weeks), and Figure (d) are related to the straightened hair in the second return of the volunteer (after 5 weeks).

In the application day, the experts have considered the hair treated by the composition of the present invention to be differentiated, being superior in attributes related to cosmeticity such as softness of the hair, coating (better coverage of the hair), combing of the hair and better touch of the hair, when compared to the hair treated with compositions of the state of the art.

In the first return, the volunteers' hair showed tendency to have a better appearance, with more discipline after the touch, and did not present performance inferior to the reference in none of the evaluated aspects.

In the second return, the tested formula presented performance paired with reference in all evaluated criteria.

It was found that the inventive formula significantly straightened the hair from a curly state in both returns of the volunteers (after 2 weeks and after 5 weeks), imparted excellent discipline to the hair (i.e., very low amount of or no frizz) and significantly reduced the volume of the hair.

The composition of the present invention presented a superior performance to the reference on the day of application, and paired performance in the returns.

Example 11

Stability Studies

For the analysis of the stability of the compositions of the present invention, all compositions were placed in storage up to 2 months at different temperature conditions: 4° C., 25° C. (room temperature) and 45° C. At the end of each month, samples of each composition were taken, and their physicochemical properties were analyzed (color, odor, aspect, pH, viscosity and amount of hydrogen peroxide).

To be considered as "stable", the compositions should present, at the end of each month, the same properties of the date of manufacture. In other words, if the sample placed at 45° C. for 2 months is stable, it is an indication that the product will be stable for 3 years at room temperature.

At all the analyzed stages, the composition of the present invention proved to be stable, as demonstrated by the table below.

TABLE 2

| EXAMPLE | CONDITION | DOSAGE | DOSAGE RANGE | pH | PH RANGE | VISCOSITY | VISCOSITY RANGE |
|---|---|---|---|---|---|---|---|
| Ex. 2 | After 2 months - 25° C. | 2.01% | 2.18-2.52% | 2.56 | | 30 P | |
| | After 2 months - 4° C. | 1.89% | | 2.84 | | 12 P | |
| | After 2 months - 45° C. | 1.80% | | 2.93 | | 27.5 P | |
| Ex. 3 | After 2 months - 25° C. | 2.15% | 2.18-2.52% | 2.65 | 2.2-2.7 | 16.6 P | 12.4 P to 21.3 P |
| | After 2 months - 4° C. | 2.19% | | 2.58 | | 15.5 P | (30-50 UD) |
| | After 2 months - 45° C. | 2.23% | | 2.75 | | 20 P | |
| Ex. 4 | After 2 months - 25° C. | 2.23% | 2.18-2.52% | 2.65 | | 20.5 P | |
| | After 2 months - 4° C. | 2.21% | | 2.60 | | 21.1 P | |
| | After 2 months - 45° C. | 2.18% | | 2.68 | | 22 P | |
| Ex. 5 | After 2 months - 25° C. | 2.24% | 2.18-2.52% | 2.58 | | 21 P | |
| | After 2 months - 4° C. | 2.18% | | 2.53 | | 17.1 P | |
| | After 2 months - 45° C. | 2.16% | | 2.55 | | 20 P | |
| Ex. 6 | After 2 months - 25° C. | 2.10% | 2.18-2.52% | 2.48 | | 22 P | |
| | After 2 months - 4° C. | 2.17% | | 2.55 | | 20.3 P | |
| | After 2 months - 45° C. | 2.11% | | 2.63 | | 20.8 P | |
| Ex. 7 | After 2 months - 25° C. | 2.16% | 2.18-2.52% | 2.58 | | 20.2 P | |
| | After 2 months - 4° C. | 2.17% | | 2.70 | | 19 P | |
| | After 2 months - 45° C. | 2.15% | | 2.78 | | 20.4 P | |
| Ex. 8 | After 2 months - 25° C. | 2.17% | 2.18-2.52% | 2.60 | | 13.7 P | |
| | After 2 months - 4° C. | 2.19% | | 2.58 | | 12.4 P | |
| | After 2 months - 45° C. | 2.16% | | 2.72 | | 15 P | |

As demonstrated by Table 2, the compositions according to the present invention (Ex. 3 to 8) were considered as stable, since the measured physicochemical parameters did not vary after 2 months at the temperatures of 4° C., 25° C. (room temperature) and 45° C. On the other hand, the composition according to the state of the art (Ex. 2) were not considered as stable.

Example 12

Standard Reducing Composition

An Example of a standard reducing composition for shaping or altering the shape of hair is as follows:

TABLE 3

Standard Reducing Composition According to the State of the Art

| INGREDIENT | AMOUNT |
|---|---|
| PPG-5-ceteth-20 | 3 |
| Mineral oil | 4 |
| Cetearyl alcohol (and) ceteth-10 phosphate | 3.5 |
| Cetearyl alcohol | 5.0 |
| Thioglycolic acid | 9 |
| Ethanolamine | 12.8 |
| EDTA | 0.1 |
| Diammonium dithiodiglycolate | 1.0 |
| Ammonium bicarbonate | 2.30 |
| Fragrance | 0.60 |
| Water | QS to 100 |

The invention claimed is:
1. A composition for shaping or altering the shape of hair, comprising:
 (a) about 0.65 to about 3.4 wt. % of hydrogen peroxide;
 (b) about 0.4 to about 10 wt. % of dipropylene glycol, and optionally at least one additional stabilizing agent selected from propylene glycol, glycerin, caprylyl glycol, or mixtures thereof;
 (c) about 0.03 to about 1 wt. % of tetrasodium etidronate, tetrasodium pyrophosphate, and sodium salicylate;
 (d) about 0.5 to about 5 wt. % of at least one cationic surfactant selected from alkyl quaternary ammonium compounds, fatty dialkylamines, fatty amidoamine compounds, or mixtures thereof; and (e) about 50 to about 90 wt. % of water;

wherein the composition is stable for at least 2 months at 45° C. and all percentages by weight are based on a total weight of the composition.

2. The composition according to claim 1, wherein the composition has a pH from 2 to less than 7.

3. The composition according to claim 1, wherein the composition has a viscosity of 12.4 P to 21.3 P (30 to 50 UD).

4. The composition according to claim 1, wherein the hydrogen peroxide is in an amount of about 1.5 to about 3 wt. %.

5. The composition according to claim 1, wherein the dipropylene glycol is in an amount of about 0.45 to about 8 wt. %.

6. The composition according to claim 1 comprising the at least one additional stabilizing agent selected from propylene glycol, glycerin, caprylyl glycol, or mixtures thereof.

7. The composition according to claim 6, wherein the at least one additional stabilizing agent is glycerin.

8. The composition according to claim 1, wherein the tetrasodium etidronate, tetrasodium pyrophosphate, and sodium salicylate are in an amount of 0.06 to 0.6 wt. %.

9. The composition according to claim 1, wherein at least one of the tetrasodium etidronate, tetrasodium pyrophosphate, and sodium salicylate is in an amount of 0.01 to 0.6 wt. %.

10. The composition according to claim 1, wherein at least one of the tetrasodium etidronate, tetrasodium pyrophosphate, and sodium salicylate is in an amount of 0.01 to 0.5 wt. %.

11. The composition according to claim 1, wherein at least one of the tetrasodium etidronate, tetrasodium pyrophosphate, and sodium salicylate is in an amount of 0.01 to 0.3 wt. %.

12. The composition according to claim 1, wherein the at least one cationic surfactant is selected from alkyl quaternary ammonium compounds.

13. The composition according to claim 12, wherein the at least one cationic surfactant is selected from behentrimonium chloride, cetrimonium chloride, behentrimonium methosulphate, or mixtures thereof.

14. The composition according to claim 1, wherein the composition further comprises at least one additional ingredient selected from thickening agents, conditioning agents, natural and synthetic oils, humectants, shine agents, fillers, colorants, pigments, chelating agents, sequestering agents, fragrances, preservatives, stabilizers, silicones, polymers, vitamins, surfactants, buffers, or mixtures thereof.

15. The composition according to claim 1, wherein the water is in an amount of about 60 to about 95 wt. %.

16. The composition according to claim 1, wherein the composition is in the form of an O/W emulsion.

17. A method for shaping or altering the shape of hair comprising:
(a) contacting hair with a shampoo having a neutral pH;
(b) drying the hair;
(c) applying onto the hair a reducing composition;
(d) leaving the standard reducing composition onto the hair for approximately 30 minutes;
(e) rinsing the hair with water;
(f) drying the hair;
(g) straightening the hair;
(h) applying onto the hair the composition of claim 1;
(i) leaving the composition into the hair for approximately 1 to 60 minutes;
(j) rinsing the hair with water;
(k) washing the hair with an intermediate agent having a neutral pH and selected from a shampoo, a conditioner, or a combination thereof, followed by rinsing with water.

18. The method according to claim 17, wherein in step (i) the composition is left into the hair for 5 to 30 minutes.

19. The composition of claim 7, wherein the at least one cationic surfactant is behentrimonium chloride.

* * * * *